US00PP37678P2

(12) United States Plant Patent
Heuger

(10) Patent No.: US PP37,678 P2
(45) Date of Patent: Sep. 8, 2026

(54) ***HELLEBORUS* PLANT NAMED 'HL 1060'**

(50) Latin Name: ***Helleborus* x *niger* X *Helleborus* x *hybridus***
Varietal Denomination: HL 1060

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 19/397,963

(22) Filed: Nov. 23, 2025

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Helleborus* plant named 'HL 1060', characterized by its upright to outwardly spreading and mounded plant habit; moderately vigorous to vigorous growth habit; dark green-colored leaflets; freely flowering habit; flowers with white and light purple-colored petals and purplish pink-colored sepals; and good garden performance.

2 Drawing Sheets

Figure 1:
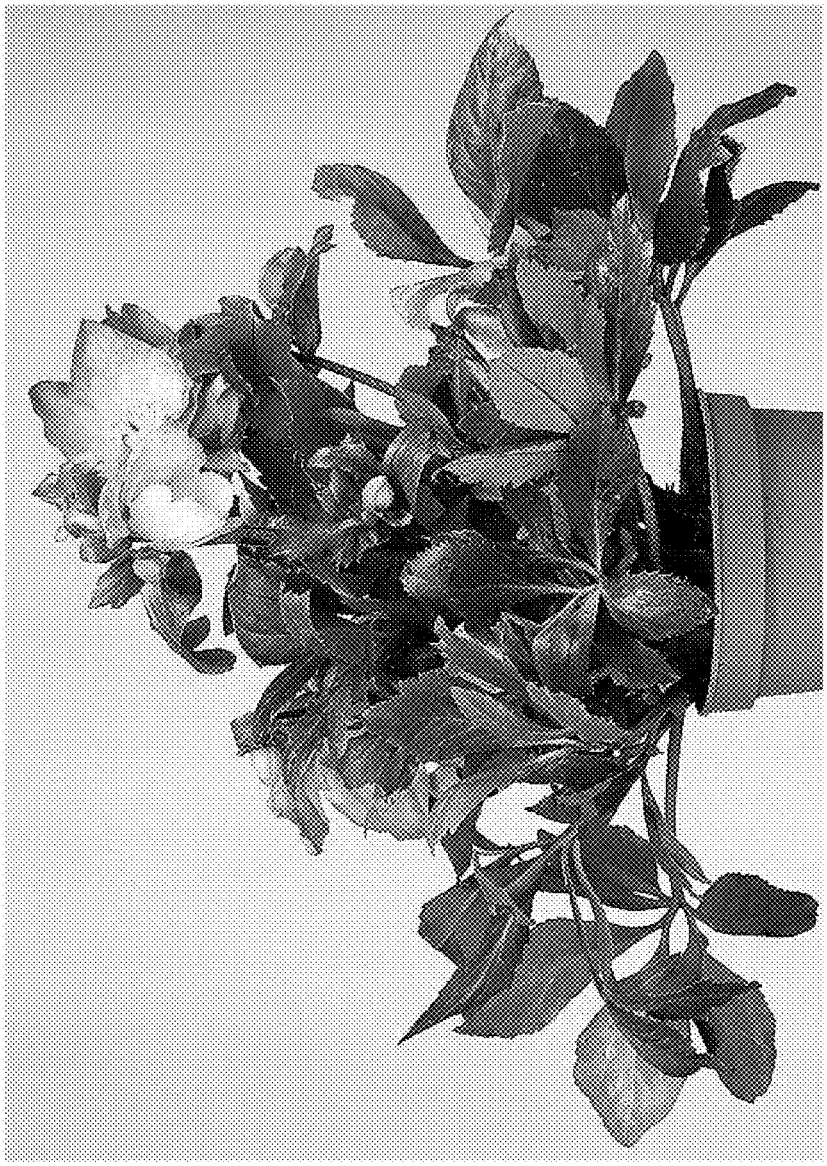

Botanical designation: *Helleborus* x *niger* X *Helleborus* x *hybridus*.

Cultivar denomination: 'HL 1060'.

CROSS-REFERENCED TO CLOSELY-RELATED APPLICATIONS

A European Community Plant Breeder's Rights application for the instant plant was filed by the Inventor/Applicant, Mr. Josef Heuger of Glandorf, Germany, on Nov. 30, 2024, application number 2024/2904. Foreign priority is not claimed to this application.

A United Kingdom Plant Breeder's Rights application for the instant plant was filed by the Inventor/Applicant, Mr. Josef Heuger of Glandorf, Germany, on Aug. 29, 2025, application number 30/987. Foreign priority is not claimed to this application.

BACKGROUND OF THE INVENTION

The present invention relates to a new and distinct cultivar of *Helleborus* plant, botanically known as *Helleborus* x *niger* X *Helleborus* x *hybridus* and hereinafter referred to by the name 'HL 1060'.

The new *Helleborus* plant is a product of a planned breeding program conducted by the Inventor in Glandorf, Germany. The objective of the breeding program was to create new uniform *Helleborus* plants with unique leaf and flower coloration and tolerance to biotic and abiotic stresses.

The new *Helleborus* plant originated from a cross-pollination conducted by the Inventor in Glandorf, Germany in December, 2017 of a proprietary selection of *Helleborus* x *niger* identified as code number 780, not patented, as the female, or seed, parent and a proprietary selection of *Helleborus* x *hybridus* identified as code number 16-32, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in November, 2019.

Asexual reproduction of the new *Helleborus* plant by in vitro axillary meristem culture in a controlled environment in Glandorf, Germany since December, 2020 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1060'. These characteristics in combination distinguish 'HL 1060' as a new and distinct *Helleborus* plant:

1. Upright to outwardly spreading and mounded plant habit.
2. Moderately vigorous to vigorous growth habit.
3. Dark green-colored leaflets.
4. Freely flowering habit.
5. Flowers with white and light purple-colored petals and purplish pink-colored sepals.
6. Good garden performance.

Plants of the new *Helleborus* differ from plants of the female parent selection in the following characteristics:

1. Petals of plants of the new *Helleborus* are not transformed into nectaries whereas petals of plants of the female parent selection are transformed into nectaries.
2. Flower sepals of plants of the new *Helleborus* are purplish pink in color whereas flower sepals of plants of the female parent selection are white in color.

Plants of the new *Helleborus* differ from plants of the male parent selection in the following characteristics:

1. Plants of the new *Helleborus* are more compact than plants of the male parent selection.
2. Flower sepals of plants of the new *Helleborus* are purplish pink in color whereas flower sepals of plants of the male parent selection are red in color.

Plants of the new *Helleborus* can also be compared to plants of *Helleborus* x *niger* X *Helleborus* x *hybridus* 'COSEH 5900', disclosed in U.S. Plant Pat. No. 32,340. In side-by-side comparisons, plants of the new *Helleborus* differ primarily from plants of 'COSEH 5900' in the following characteristics:

1. Petals of plants of the new *Helleborus* are not transformed into nectaries whereas petals of plants of 'COSEH 5900' are transformed into nectaries.
2. Flower sepals of plants of the new *Helleborus* are purplish pink in color whereas flower sepals of plants of 'COSEH 5900' are white in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HL 1060' grown in a container.

Figure 2:
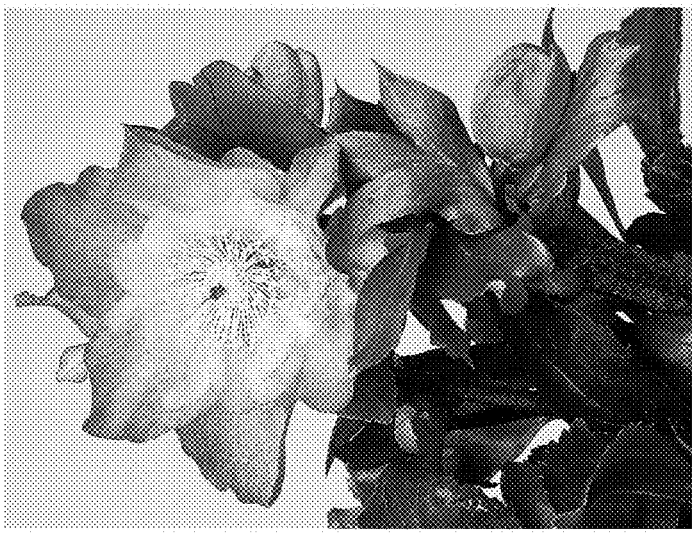

The photograph at the left of the second sheet (FIG. 2) is a close-up view of a typical flower of 'HL 1060'.

Figure 3:
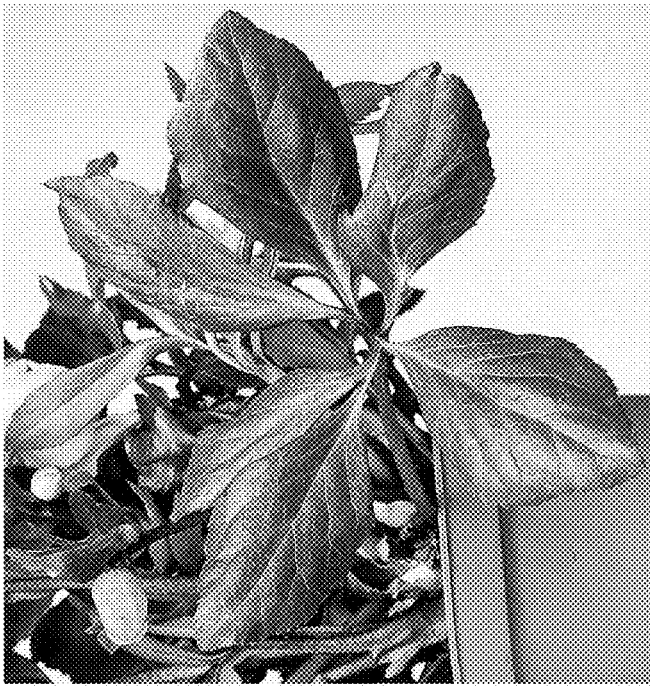

The photograph at the right of the second sheet (FIG. 3) is a close-up view of typical leaflets of 'HL 1060'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 48 weeks old when the photographs were taken and 14 months old when the detailed description was taken. In the following description, color references are made to The Royal Horticultural Society Colour Chart, Sixth Edition (2019 reprint), except where general terms of ordinary dictionary significance are used.

Botanical classification: *Helleborus* x *niger* X *Helleborus* x *hybridus* 'HL 1060'.

Parentage:

*Female, or seed, parent*.—Proprietary selection of *Helleborus* x *niger* identified as code number 780, not patented.

*Male, or pollen, parent*.—Proprietary selection of *Helleborus* x *hybridus* identified as code number 16-32, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to outwardly spreading and mounding plant habit with flowers held above the foliar plane; plant shape, roughly flattened globular to globular; moderately vigorous to vigorous growth habit and moderate growth rate.

*Plant height, soil level to top of foliar plane*.—About 26.4 cm.

*Plant height, soil level to top of flowers*.—About 36.2 cm.

*Plant diameter* (*area of spread*).—About 50.2 cm.

Leaf description:

*Arrangement*.—Leaves arranged in basal rosettes; leaves palmately compound with typically five leaflets per leaf.

*Leaf length*.—About 17 cm.

*Leaf width*.—About 21.9 cm.

*Leaflet length*.—About 13.3 cm.

*Leaflet width*.—About 6.6 cm.

*Leaf shape*.—Palmate; roughly reniform in outline.

*Leaflet shape*.—Obovate to elliptic; moderately concave; lowest leaflets are typically cleft.

*Leaflet apex*.—Acute to bluntly acute.

*Leaflet base*.—Attenuate.

*Leaflet margin*.—Serrate; slightly to moderately coarsely undulate.

*Leaflet texture and luster, upper surface*.—Smooth, glabrous; coriaceous and tough; moderately glossy.

*Leaflet texture and luster, lower surface*.—Smooth, glabrous; coriaceous and tough; slightly glossy.

*Leaflet venation pattern*.—Pinnate and reticulate.

*Leaflet color*.—Developing leaflets, upper surface: Close to 137B; towards the base, close to 183A. Developing leaflets, lower surface: Close to 146B; main veins, close to 178A. Fully developed leaflets, upper surface: Close to a blend of NN137A and 147A; venation, close to 144A and 144B. Fully developed leaflets, lower surface: Close to 147B; venation, close to between 145A and 146D.

*Petioles*.—Length: About 14.7 cm. Diameter: About 7 mm by 8 mm. Strength: Strong. Texture and luster, upper and lower surfaces: Smooth, glabrous; slightly glossy. Color, upper surface: Close to 146B with dots, close to 200B. Color, lower surface: Close to 146C with dots, close to 200B; proximally, strongly tinged with close to N186C and 200B.

Flower description:

*Flower shape and habit*.—Double rotate bowl-shaped flowers arranged in panicles; freely flowering habit with about three flowers per inflorescence and about 30 flowers and flower buds per plant; flowers face outwardly to slightly nodding.

*Fragrance*.—None detected.

*Natural flowering season*.—Plants begin flowering about ten months after planting; plants flower naturally from early winter into the late winter in Germany.

*Flower longevity on the plant*.—About ten days; sepals persistent, other flower parts are not persistent.

*Flower buds*.—Length: About 2.5 cm. Diameter: About 1.7 cm. Shape: Ovate. Texture and luster: Smooth, glabrous; matte to slightly glossy. Color: Upper surface, close to 183D; lower surface, close to 182C, 182D and 155A.

*Inflorescence height* (*including peduncle*).—About 33.4 cm.

*Inflorescence diameter*.—About 15 cm.

*Flower diameter*.—About 9.8 cm.

*Flower depth*.—About 5 cm.

*Petals*.—Quantity and arrangement: About 12 to 16, arranged in a single whorl. Length: About 4.9 cm. Width: About 2.1 cm. Shape: Obovate to elliptic. Apex: Obtuse to bluntly acute. Base: Attenuate. Margin: Entire; not undulate. Texture and luster, upper surface: Smooth, glabrous; matte. Texture and luster, lower surface: Smooth, glabrous; slightly glossy. Color: When opening, upper and lower surfaces: Close to NN155C; at the base, close to 146D tinged with close to 184D. Fully opened, upper surface: Close to NN155B; apical and marginal edges, tinged with close to 75C; at the base, close to 145A; with subsequent development, color becoming closer to 147C with apical and marginal edges, closer to 183C and 183D. Fully opened, lower surface: Close to N155B; distally, flushed with close to 186C; towards the base, strongly flushed with close to 70B; at the base, close to 152C and 152D; with subsequent development, color becoming closer to 148B tinged with close to 183C.

*Sepals*.—Quantity and arrangement: About five, arranged in a single whorl. Length: About 7 cm. Width: About 5.2 cm. Shape: Broadly ovate to broadly elliptic; slightly concave. Apex: Obtuse. Base: Cuneate. Margin: Entire. Texture and luster, upper surface: Smooth, glabrous; matte. Texture and luster, lower surface: Smooth, glabrous; slightly glossy. Color: When opening, upper surface: Close to 76D; towards the apex and margins, close to 186C and 186D; at the base, close to 145A. When opening, lower surface: Close to 186B and 186C; towards the apex, flushed with close to N199A; towards the base, flushed with close to N199B; at the base, close to 146D. Fully opened, upper surface: Close to 186D; towards the apex and margins, close to 186C; at the apex, flushed with close to N148B; at the base, close to 145B. Fully opened, lower surface: Close to 186B and 186C; proximal margins, close to 186D; towards the apex, flushed with close to 152B; towards the base, flushed with close to 183C; at the base, close to 152B.

*Flower bracts*.—Quantity per flower: Typically one or two. Length: About 9.5 cm. Width: About 5.2 cm. Shape: Ovate. Apex: Acute. Base: Truncate to cuneate. Margin: Entire and distally, serrate; coarsely undulate. Color, upper surface: Close to NN137A. Color, lower surface: Close to a blend of 146B and 147B; venation, close to 183B.

*Peduncles*.—Length: About 23.3 cm. Diameter: About 7 mm to 8 mm. Aspect: About 20° from vertical. Strength: Strong. Texture and luster: Smooth, glabrous; moderately glossy. Color: Close to 146C; heavily covered with fine dots, close to 187B.

*Pedicels*.—Length: About 5.4 cm. Diameter: About 4 mm. Aspect: About 20° from peduncle axis. Strength: Moderately strong. Texture and luster: Smooth, glabrous; moderately glossy. Color: Close to 146D; heavily covered with fine dots, close to 187C.

*Reproductive organs*.—Stamens: Quantity per flower: About 150. Filament length: About 2.2 cm. Filament color: Close to 155A. Anther shape: Double and broadly reniform; basifixed. Anther size: About 2 mm by 3 mm. Anther color: Close to 154C to 154D. Pollen amount: Sparse. Pollen color: Close to 4D. Pistils: Quantity per flower: About two to seven. Pistil length: About 1 cm. Stigma diameter: About 0.3 mm. Stigma shape: Club-shaped. Stigma color: Close to 157D. Style length: About 0.95 cm. Style color: Close to 184A. Ovary color: Close to 152D with fine dots, close to 184D. Seeds and fruits: To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1060' as herein illustrated and described.

* * * * *